(12) United States Patent
Nishizawa et al.

(10) Patent No.: US 9,414,829 B2
(45) Date of Patent: Aug. 16, 2016

(54) MEDICAL PORT

(71) Applicant: OLYMPUS CORPORATION, Tokyo (JP)

(72) Inventors: Koji Nishizawa, Tokyo (JP); Kazuo Banju, Tokyo (JP); Takahiro Kogasaka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 34 days.

(21) Appl. No.: 13/937,452

(22) Filed: Jul. 9, 2013

(65) Prior Publication Data

US 2014/0018630 A1    Jan. 16, 2014

Related U.S. Application Data

(63) Continuation of application No. PCT/JP2012/082801, filed on Dec. 18, 2012.

(60) Provisional application No. 61/579,118, filed on Dec. 22, 2011.

(51) Int. Cl.
*A61B 17/34* (2006.01)
*A61B 17/02* (2006.01)
*A61B 1/00* (2006.01)

(52) U.S. Cl.
CPC ......... *A61B 17/0218* (2013.01); *A61B 1/00131* (2013.01); *A61B 1/00098* (2013.01); *A61B 17/0293* (2013.01); *A61B 2017/3445* (2013.01); *A61B 2017/3452* (2013.01); *A61B 2017/3466* (2013.01); *A61B 2017/3484* (2013.01)

(58) Field of Classification Search
CPC ........... A61B 17/3423; A61B 17/0293; A61B 17/3452; A61B 17/3466; A61B 17/3484; A61B 17/31
See application file for complete search history.

(56) References Cited

U.S. PATENT DOCUMENTS 6,551,270 B1 * 4/2003 Bimbo ............... A61B 17/3421
                                                             604/167.03
2005/0228447 A1    10/2005 Rambo
2006/0247498 A1 * 11/2006 Bonadio et al. ............... 600/208
(Continued)

FOREIGN PATENT DOCUMENTS

EP        1 591 069 A1    11/2005
JP        A-11-169342      6/1999
(Continued)

OTHER PUBLICATIONS

International Search Report issued in International Patent Application No. PCT/JP2012/082801 dated Jan. 29, 2013 (w/ translation).
(Continued)

*Primary Examiner* — Samuel Hanna
(74) *Attorney, Agent, or Firm* — Oliff PLC

(57) ABSTRACT

A medical port includes: a faceplate having a through-hole; a fixing ring formed in an annular shape and having an outer circumferential surface in which an outer diameter is gradually increased from a first opening end opened at a faceplate side toward a second opening end opened at an opposite side of the faceplate side; and a moving member connected to the fixing ring and the faceplate and configured to move the fixing ring with respect to the faceplate such that the fixing ring is pulled toward the faceplate.

6 Claims, 13 Drawing Sheets

(56) References Cited

U.S. PATENT DOCUMENTS

| | | | |
|---|---|---|---|
| 2009/0036745 A1* | 2/2009 | Bonadio et al. | 600/208 |
| 2009/0187079 A1 | 7/2009 | Albrecht et al. | |
| 2009/0227843 A1* | 9/2009 | Smith et al. | 600/208 |
| 2011/0071359 A1* | 3/2011 | Bonadio | A61B 17/3423 600/184 |

FOREIGN PATENT DOCUMENTS

| | | |
|---|---|---|
| JP | A-2008-515523 | 5/2008 |
| JP | A-2011-67598 | 4/2011 |
| JP | A-2011-83605 | 4/2011 |
| WO | WO 2004/066848 A1 | 8/2004 |
| WO | WO 2006/040748 A1 | 4/2006 |
| WO | 2011/153548 A1 | 12/2011 |

OTHER PUBLICATIONS

Aug. 14, 2015 Search Report issued in European Patent Application No. 12858897.7.

* cited by examiner

MEDICAL PORT

This application is a continuation application based on a PCT Patent Application No. PCT/JP2012/082801, filed Dec. 18, 2012, whose priority is claimed on U.S. Provisional Patent Application No. 61/579,118, filed Dec. 22, 2011. The contents of both the PCT Application and US Application are incorporated herein by reference.

BACKGROUND OF THE INVENTION

1. Field of the Invention

The present invention relates to a medical port.

2. Description of Related Art

In the related art, in surgical treatment in the digestive tract or another body cavity, medical devices such as an endoscope device, a treatment tool, or the like, may be inserted into the digestive tract or the body cavity to perform the treatment. In such a surgical treatment, in order to secure an operative field for observation or remedy of a treatment target portion using the medical devices and effectively guide a plurality of medical devices to the treatment target portion, a medical port configured to assist with insertion of these medical devices is used.

The medical port attached to a natural opening such as the anus or the like (for example, see Japanese Unexamined Patent Application, First Publication No. H11-169342) or attached to a cutout portion of a body cavity surface (for example, Japanese Unexamined Patent Application, First Publication No. 2011-067598) is known.

SUMMARY OF THE INVENTION

According to a first aspect of the present invention, a medical port includes: a faceplate having a through-hole through which a medical device is capable of being inserted; a fixing ring having an internal space into which the medical device passing through the through-hole is capable of being inserted, and an outer circumferential surface, the fixing ring being formed in an annular shape, an outer diameter of the outer circumferential surface being gradually increased from a first opening end which is in communication with the internal space and is opened at a faceplate side toward a second opening end which is in communication with the internal space and is opened at a side opposite to the faceplate side; and a moving member connected to the fixing ring and the faceplate, the moving member being configured to move the fixing ring with respect to the faceplate such that the fixing ring is pulled toward the faceplate.

According to a second aspect of the present invention, in the medical port according to the first aspect, an inner diameter of at least one of the first opening end and the second opening end may be smaller than an outer diameter of the faceplate.

According to a third aspect of the present invention, in the medical port according to the first aspect, the fixing ring may be elastically deformable.

According to a fourth aspect of the present invention, in the medical port according to the first aspect, the fixing ring may be an elastic member formed in a C shape when seen from a direction of a central axis of the fixing ring. The fixing ring may further have a string-shaped member which is fixed to a first end in a circumferential direction of the fixing ring and which is inserted into a second end in the circumferential direction of the fixing ring. The string-shaped member may be drawn from a surface of the faceplate opposite to a surface thereof directed toward the fixing ring.

According to a fifth aspect of the present invention, in the medical port according to the first aspect, the faceplate may include: a main body having a disc shape, the through-hole being formed in the main body; and a fixing plate connected to the main body such that a gap is formed between the fixing plate and an outer circumferential surface of the main body in a state in which movement of the fixing plate with respect to the main body in a direction of the central axis of the main body is restricted. The moving member may be a flexible tubular member, a first end of the moving member being fixed to any one of the fixing plate and the main body. The tubular member may be formed in a double tube shape in which an inner surface and an outer surface are turned to be interchanged at a halfway portion in an extending direction of the tubular member. In an inner tube and an outer tube of the tubular member, provided that a tube including the first end of the moving member is referred to as a first tube and a tube that does not include the first end of the moving member is referred to as a second tube, the second tube may be inserted into the gap of the faceplate. The fixing ring may be disposed in a space between the first tube and the second tube.

According to a sixth aspect of the present invention, in the medical port according to the first aspect, an air supply conduit extending substantially in parallel to a direction of the central axis of the faceplate, and an air suction conduit extending substantially in parallel to the direction of the central axis of the faceplate may be formed in the through-hole. A position of an opening of the air supply conduit directed in a direction from the faceplate toward the fixing ring and a position of an opening of the air suction conduit directed in the direction from the faceplate toward the fixing ring may be offset to each other in the direction of the central axis of the faceplate.

DETAILED DESCRIPTION OF THE INVENTION (Medical Port)

Figure 1:
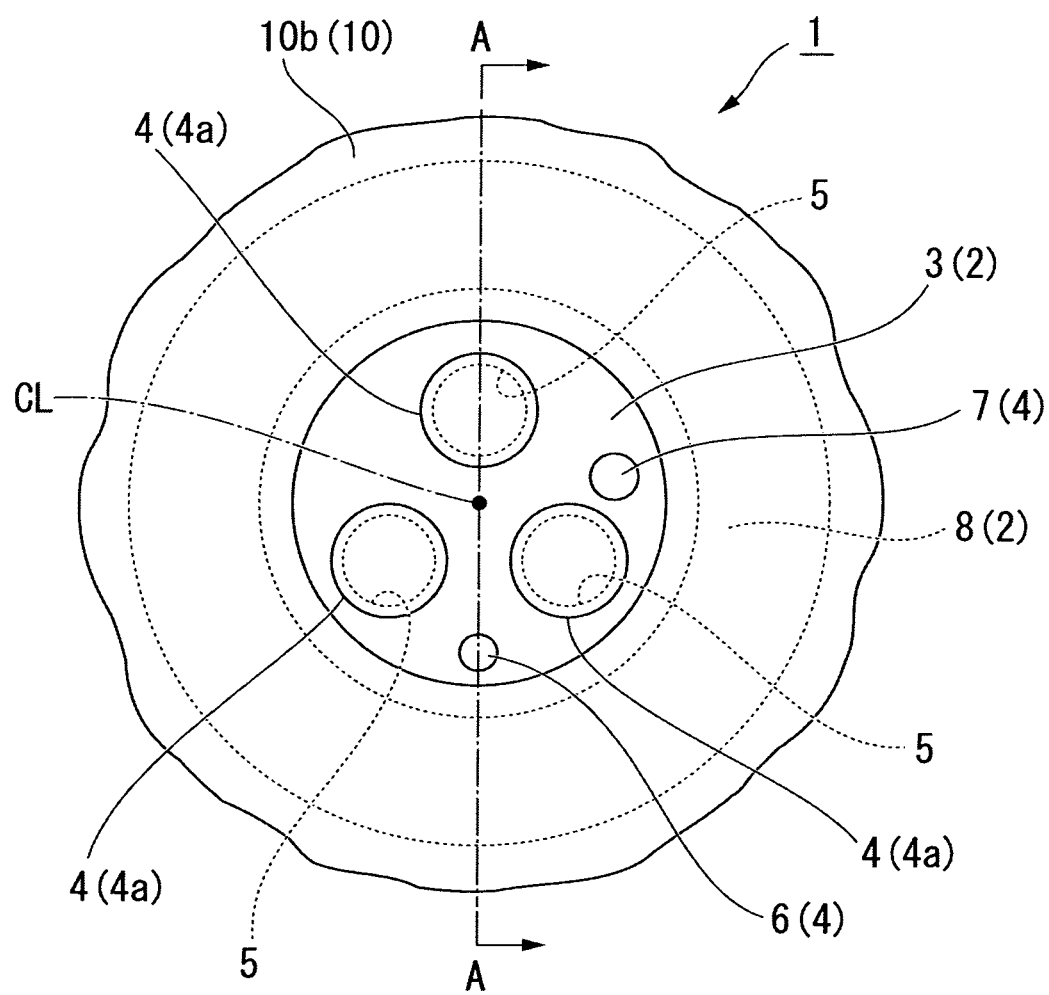
FIG. 1 is a front view of a medical port according to an embodiment of the present invention.
Figure 2:
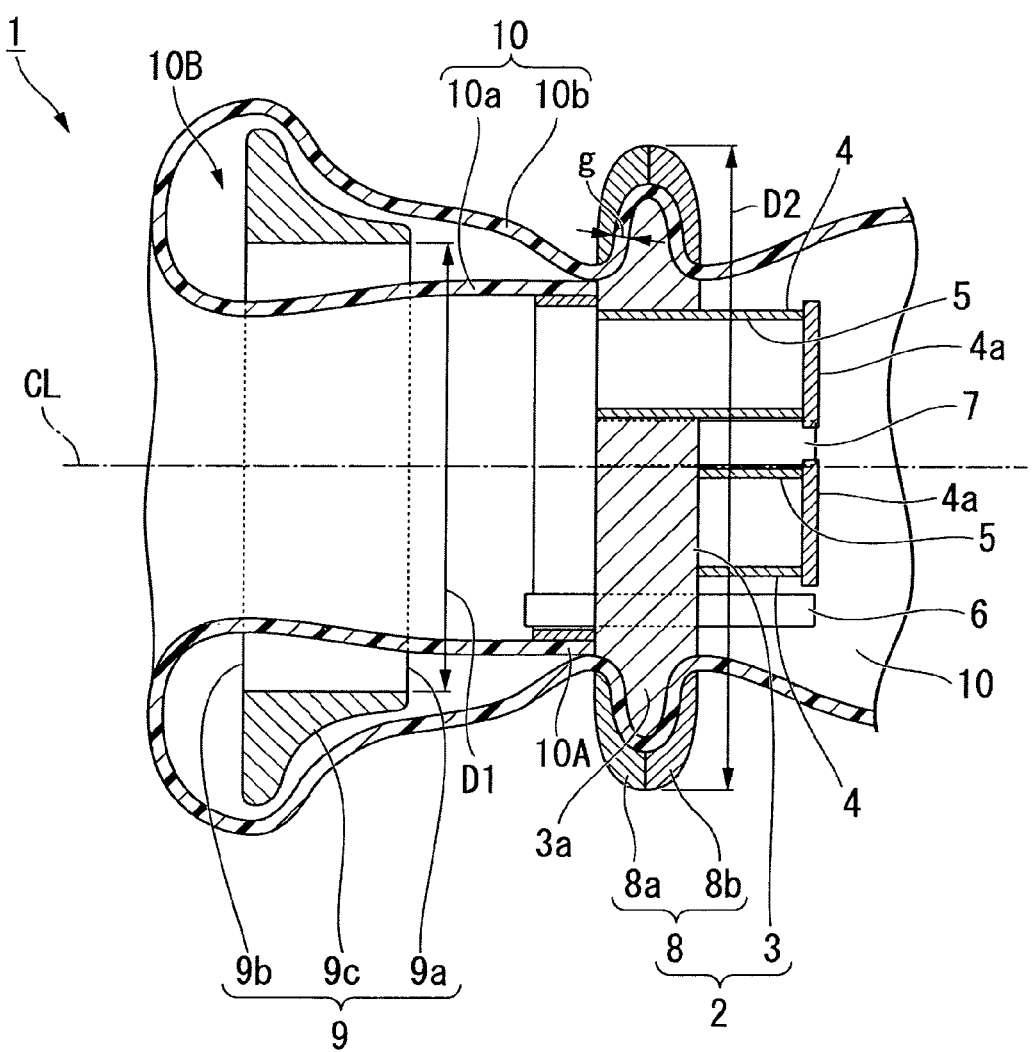
FIG. 2 is a cross-sectional view taken along a line A-A of FIG. 1.
Figure 3A:
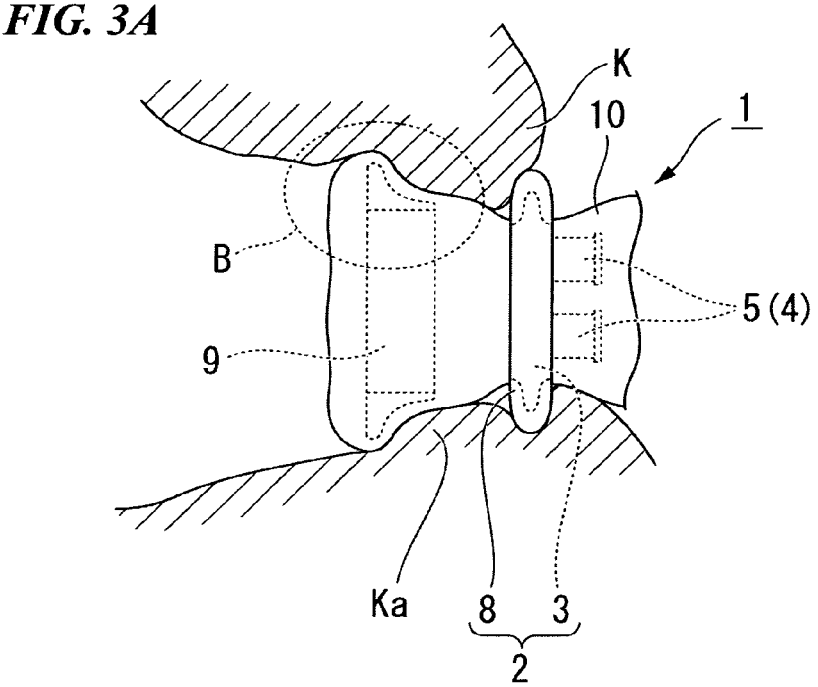
FIG. 3A is an explanatory view showing a process upon use of the medical port according to the embodiment of the present invention.
Figure 3B:
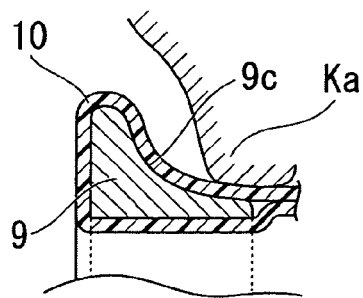
FIG. 3B is a view of a process upon use of the medical port according to the embodiment of the present invention, showing a cross-sectional view of a portion B of FIG. 3A.
Figure 3C:
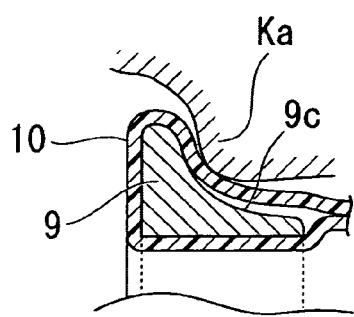
FIG. 3C is a view of a process upon use of the medical port according to the embodiment of the present invention, showing a cross-sectional view of the portion B of FIG. 3A.

A medical port according to an embodiment of the present invention is described. FIG. 1 is a front view of the medical port according to the embodiment of the present invention. FIG. 2 is a cross-sectional view taken along a line A-A of FIG. 1. FIGS. 3A, 3B, and 3C are explanatory views showing a process upon use of the medical port according to the embodiment of the present invention.

The medical port according to the present embodiment is optimized to be appropriately attached to an anus.

As shown in FIGS. 1 and 2, a medical port 1 includes a faceplate 2, a fixing ring 9, and a moving member 10.

The faceplate 2 includes a main body 3, and a fixing plate 8. The main body 3 has a disc shape. The fixing plate 8 is connected to a circumference of the main body 3 via the moving member 10.

At least one port section (a through-hole) 4 passing through the faceplate 2 in a thickness direction of the faceplate 2 is formed in the faceplate 2. In the medical port 1, for example, five port sections 4 are formed in the main body 3 of the faceplate 2. In addition, the constitution of the faceplate 2 is not limited to the above-mentioned constitution.

A circular projection section 3a protruding outward in a radial direction of the main body 3 is formed at an outer circumferential surface of the main body 3. Device insertion holes 5 through which medical devices (not shown) are inserted are formed at three of the port sections 4. Each of the device insertion holes 5 is sealed by a cap 4a. The device insertion holes 5 are configured such that the medical devices can be inserted into the device insertion hole 5 in a state in which the caps 4a are removed or the medical devices can be inserted into slits (not shown) formed in the caps 4a upon use of the device insertion hole 5.

As the constitution of the port section 4, known constitutions can be appropriately selected and employed to correspond to content of a technique to which the medical port 1 is applied. In the medical port 1, as the port section 4, in addition to the constitution in which the device insertion hole 5 is formed, an air supply conduit 6 and an air suction conduit 7 extending substantially in parallel to a central axis CL of the faceplate 2 are formed in the faceplate 2.

A position of an opening of the air supply conduit 6 in a direction from the faceplate 2 toward the fixing ring 9 and a position of an opening of the air suction conduit 7 in the direction from the faceplate 2 toward the fixing ring 9 are offset from each other when seen from a direction of the central axis CL of the faceplate 2. In the medical port 1, the position of the opening of the air suction conduit 7 in the direction from the faceplate 2 toward the fixing ring 9 is closer to the faceplate 2 than the position of the opening of the air supply conduit 6 in the direction from the faceplate 2 toward the fixing ring 9.

The fixing plate 8 is an annular member formed by concentrically combining a first member 8a and a second member 8b formed in an annular shape with each other. The circular projection section 3a formed at the outer circumferential section of the main body 3 is inserted into a space formed between the first member 8a and the second member 8b. Further, a gap g is formed between the fixing plate 8 and the circular projection section 3a. The gap g is formed such that the fixing plate 8 is rotatable with respect to the main body 3 in a circumferential direction of the main body 3. The relative position between the fixing plate 8 and the main body 3 in the circumferential direction is not fixed. That is, the fixing plate 8 is formed to have the gap g between the outer circumferential surface of the main body 3 and the fixing plate 8 in a state in which movement of the fixing plate 8 with respect to the main body 3 in the direction of the central axis CL of the main body 3 is restricted. A portion of a tubular member, which is the moving member 10 (to be described below), is inserted into the gap g between the main body 3 and the fixing plate 8.

The fixing ring 9 is an annular member separately formed from the faceplate 2. In the fixing ring 9, an inner diameter D1 of at least one opening end (a first opening end) 9a is smaller than an outer diameter D2 of the faceplate 2. Accordingly, when the fixing ring 9 and the faceplate 2 are concentrically disposed, the faceplate 2 is not inserted into the opening of the fixing ring 9.

The fixing ring 9 has a tapered outer circumferential surface 9c having an outer diameter gradually increased from the one opening end 9a toward the other opening end (a second opening end) 9b. Further, in the fixing ring 9, in a state in which both the fixing ring 9 and the faceplate 2 are connected to the moving member 10, the opening end (the one opening end 9a) of the outer circumferential surface 9c having a small outer diameter is directed toward the faceplate 2.

The fixing ring 9 can be elastically deformed. That is, the outer shape of the fixing ring 9 can be squashed to become smaller than the inner diameter of the anus. After the fixing ring 9 is squashed, as an external force applied to the fixing ring 9 is released, the fixing ring 9 is restored to an annular shape having the outer diameter larger than the inner diameter of the anus. In addition, the constitution of the fixing ring 9 is not limited to the above-mentioned constitution.

The moving member 10 is connected to the faceplate 2 and the fixing ring 9. The moving member 10 moves the fixing ring 9 with respect to the faceplate 2 such that the fixing ring 9 is pulled toward the faceplate 2. The moving member 10 is a flexible tubular member having one end 10A fixed to the main body 3. The moving member 10 is formed in a double tube shape in which an inner surface and an outer surface are turned to be interchanged at a halfway portion in the longitudinal direction of the moving member 10. Vinyl or the like may be used as a material of the tubular member. In an inner tube 10a and an outer tube 10b of the tubular member, which is a double tube shape, the outer tube 10b is inserted into the gap g between the main body 3 and the fixing plate 8 in the faceplate 2. The fixing ring 9 is disposed in an annular space 10B formed between the inner tube 10a and the outer tube 10b in the tubular member, which is the double tube shape. As the fixing ring 9 is accommodated in the space 10B, the fixing ring 9 is held in a state in which the opening end 9a of the fixing ring 9 having a small outer diameter is directed toward the faceplate 2. In addition, the constitution of the moving member 10 is not limited to the above-mentioned constitution.

Next, a use method and an operation of the medical port 1 according to the embodiment are described.

As shown in FIGS. 1 and 2, in the medical port 1, the faceplate 2 and the fixing ring 9 are connected by the tubular member, which is the moving member 10.

A user inserts the fixing ring 9 from the anus K into the rectum of a patient (see FIG. 3A) by pressing the fixing ring 9 via a tube 10b of the moving member 10 or using a tubular insertion assisting tool (not shown) in which the fixing ring 9 is disposed in a state in which the fixing ring 9 is previously squashed. The fixing ring 9 inserted into the rectum is restored to its original annular shape by elasticity of the fixing ring 9 itself The user positions and holds the faceplate 2 to the outside of the anus K. In addition, the user pulls the outer tube 10b drawn from between the main body 3 and the fixing plate 8 such that the outer tube 10b is further drawn from therebetween. Accordingly, the fixing ring 9 is moved toward the anus K to be directed toward the faceplate 2 attached to the outside of the anus K by the moving member 10.

The fixing ring 9 is drawn toward the faceplate 2 in a state in which the opening end 9a having a smaller outer diameter is directed toward the faceplate 2. Accordingly, an outer surface of a section in which a diameter is reduced by the anal sphincter muscle Ka comes in contact with a tapered section of the fixing ring 9 that forms the outer circumferential surface 9c via the moving member 10. As the outer tube 10b is further pulled by the user, the anal sphincter muscle Ka is sandwiched between the fixing plate 8 and the outer circumferential surface 9c of the fixing ring 9.

The inner diameter of the anus K is individually different in every patient. For example, when the inner diameter of the patient's anus K is small, in the tapered section of the outer circumferential surface 9c of the fixing ring 9, the anal sphincter muscle Ka is sandwiched at an area at which the outer diameter is small (see FIG. 3B). On the other hand, when the inner diameter of the patient's anus K is large, in the tapered section of the outer circumferential surface 9c of the fixing ring 9, the anal sphincter muscle Ka is sandwiched at an area at which the outer diameter is large (see FIG. 3c). For this reason, there is no need to select a dimension of the medical port 1 according to an individual difference in size of the inner diameter of the anus K of the patient. In addition, it is possible to reduce the probability of giving a rise to a need to exchange the medical port 1 with a new one due to a dimensional error after attachment of the medical port 1.

When the medical port 1 is attached to the anus K, the user inserts the medical devices or the like (not shown) into the medical port 1 through the device insertion holes 5 of the port sections 4. The user performs observation, surgical treatment, or the like, needed for the patient. First, the user introduces a gas from the air supply conduit 6 into the rectum to secure a field of vision in the rectum using a pneumoperitoneum apparatus or the like. After that, the user inserts the medical devices into the port section 4 and guides them to a target portion at which the observation or treatment is performed, and performs the observation or treatment. For example, when a high frequency knife is used to incise the target portion, the field of vision may be disturbed due to smoke, steam, or the like, caused by the incision. Here, the gas is introduced from the air supply conduit 6 connected to the pneumoperitoneum apparatus, and simultaneously, the gas in the rectum is exhausted from the air suction conduit 7 connected to the pneumoperitoneum apparatus or another air suction apparatus to the outside of the rectum. Here, since the position of the opening of the air supply conduit 6 and the position of the opening of the air suction conduit 7 are offset from each other in the direction of the central axis CL of the faceplate 2, circulation of the gas in the rectum is formed by the gas that exits the air supply conduit 6 and the gas that enters the air suction conduit 7. Accordingly, the smoke, steam, or the like generated in the rectum is moved to the opening of the air suction conduit 7, and effectively exhausted through the air suction conduit 7. As a result, the field of vision in the rectum is appropriately recovered for a short time. In addition, the pneumoperitoneum apparatus may be operated to always circulate the above-mentioned gas. In this case, an extent to which the field of vision is disturbed by the smoke, steam, or the like is further reduced, and the user can continue the treatment or the like without standby time until recovery from the state in which the field of vision is disturbed.

As the observation or treatment is completed, the user removes the medical devices from the medical port 1. The user extracts the medical port 1 from the anus K in a state in which the user grasps the faceplate 2 and the outer tube 10b of the moving member 10. Here, the fixing ring 9 is elastically deformed such that the size of the fixing ring 9 is reduced to be smaller than the inner diameter of the anus K due to elasticity of the fixing ring 9 itself, and exits the anus K.

When the conventional abdominal cavity port is used in the anus, the dimension of the abdominal cavity port with respect to the inner diameter of the anus may be too small so that the abdominal cavity port comes away from the anus since the anal sphincter muscle is not sandwiched by the abdominal cavity port. On the other hand, the dimension of the abdominal cavity port may be too large so that the area corresponding to the fixing ring 9 of the medical port 1 according to the present embodiment does not enter the anus.

On the other hand, according to the medical port 1 according to the present embodiment, the anal sphincter muscle Ka can be appropriately sandwiched by the tapered section formed at the outer circumferential surface 9c of the fixing ring 9 regardless of an individual difference of the inner diameter of the anus K of the patient. Accordingly, the medical port 1 can be securely fixed to the anus K.

Since the fixing ring 9 has elasticity, even when the inner diameter of the anus K is large, or even when the inner diameter of the anus K is small, the fixing ring 9 can be easily inserted into the anus K.

Since the moving member 10 is constituted by a tubular member having a double tube shape and the fixing ring 9 is disposed between the outer tube 10b and the inner tube 10a, a direction of the fixing ring 9 is not reversed after the fixing ring 9 is inserted into the anus K. Accordingly, the tapered section formed at the outer circumferential surface 9c of the fixing ring 9 can always be directed toward the anal sphincter muscle Ka.

The position of the opening of the air supply conduit 6 directed in the direction from the faceplate 2 toward the fixing ring 9 and the position of the opening of the air suction conduit 7 directed in the direction from the faceplate 2 toward the fixing ring 9 are offset in the direction of the central axis CL of the faceplate 2. For this reason, the gas can be widely circulated in one direction in the rectum.

(Modified Example)

Figure 4:
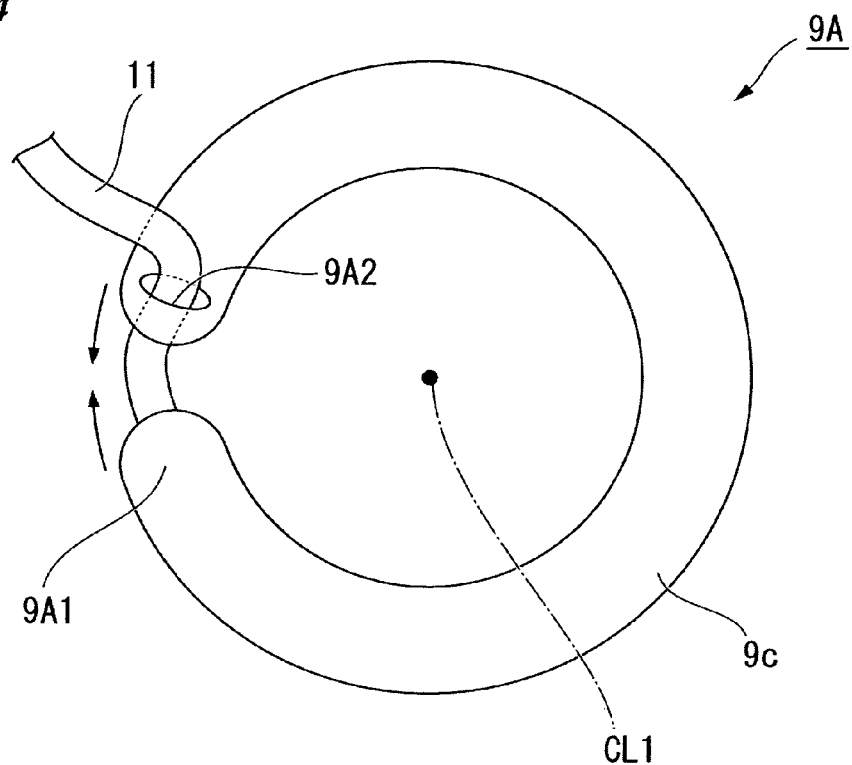
FIG. 4 is a view of a portion of a modified example of the medical port according to the embodiment of the present invention, showing a plan view of a fixing ring provided at the medical port.
Figure 5:
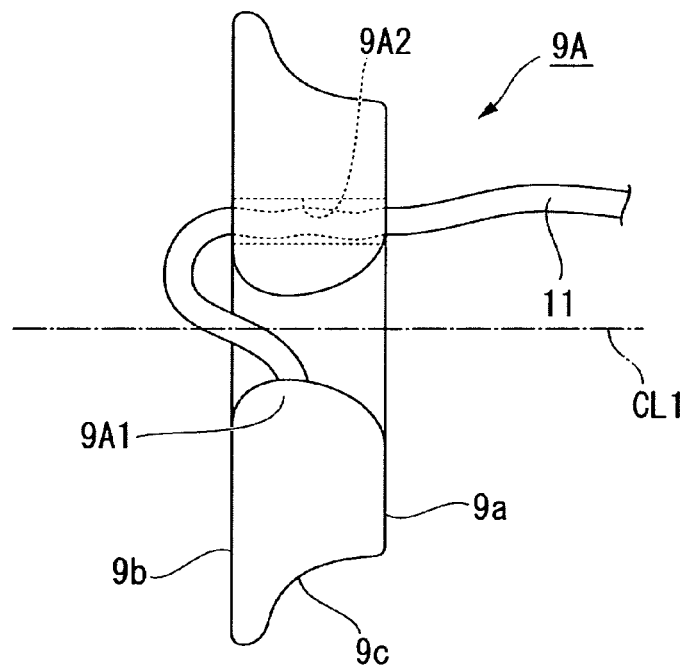
FIG. 5 is a side view of the fixing ring shown in FIG. 4.

Next, a modified example of the medical port 1 according to the above-mentioned embodiment is described. FIG. 4 is a view showing a constitution of the modified example of the medical port 1 according to the above-mentioned embodiment, showing a plan view of the fixing ring provided at the medical port. FIG. 5 is a side view of the fixing ring shown in FIG. 4. In the following description, differences between the medical port 1 according to the embodiment and the medical port of the modified example are described, the other constitutions are the same as the medical port 1 according to the embodiment, and a description thereof is not repeated here.

The medical port 1 (see FIG. 2) of the modified example is distinguished from the medical port according to the embodiment in that a fixing ring 9A having a different shape as shown in FIGS. 4 and 5 is provided instead of the fixing ring 9.

As shown in FIG. 4, the fixing ring 9A is an elastic member formed in a C shape when seen from the direction of the central axis CL1.

A distal end of a string-shaped member 11 is fixed to one end 9A1 in the circumferential direction of the fixing ring 9A. The string-shaped member 11 is inserted into a through-hole 9A2 formed in the other end in the circumferential direction of the fixing ring 9A. The string-shaped member 11 is pulled out of a surface of the faceplate 2 (see FIG. 2) opposite to a surface facing the fixing ring 9. Specifically, the string-shaped member 11 is inserted into the gap g between the main body 3 and the fixing plate 8 with the outer tube 10b of the moving member 10 while accommodated in the space 10B between the inner tube 10a and the outer tube 10b of the tubular member, which is the moving member 10.

In the modified example, after completion of the surgical treatment using the medical port 1, the string-shaped member 11 is pulled in a direction drawn from the anus K. Accordingly, the one end 9A1 in the fixing ring 9A is drawn toward the other end. Accordingly, the fixing ring 9A is reduced in diameter. As a result, the outer diameter of the fixing ring 9A is varied to an extent to which the fixing ring 9A can be removed from the anus K, and the fixing ring 9A exits the anus K.

In the above-mentioned constitution, the same effect as the medical port 1 according to the embodiment is exhibited. In addition, in the case of the modified example, the diameter of the fixing ring 9A can be actively reduced by manipulation of the string-shaped member 11. For this reason, a material harder than that of the fixing ring 9 described in the embodiment can be employed in the fixing ring 9A. Accordingly, since the fixing ring 9A is not inadvertently reduced in diameter even when the fixing ring 9A is pushed back by the anal sphincter muscle Ka, the fixing ring 9A cannot easily come away from the anus K.

The medical port 1 according to the embodiment and the medical port 1 of the modified example may have a constitution described below as an example. In the following description, while the fixing ring 9 is described, the description also applies to the fixing ring 9A.

For example, in the above-mentioned embodiment, an example using a flexible tubular member has been described as an example of the moving member 10. However, the constitution of the moving member is not limited thereto. For example, the fixing ring 9 can be drawn toward the faceplate 2 using a linear member having flexibility such as a thread, a string, a metal wire, or the like. A belt-shaped flexible tape can be employed instead of the linear member. When the linear member or the tape is employed as the moving member 10, a hole or a hook through which the linear member or the tape is inserted may be formed at the fixing ring 9. The linear member or the tape may be fixed to the fixing ring 9.

The moving member 10 may be fixed to the fixing plate 8 of the faceplate 2 instead of the main body 3 of the faceplate 2.

The fixing ring 9 may be a solid member or a hollow member. Processing for increasing the frictional force with respect to a biological tissue to which the fixing ring 9 is locked, such as the anus K or the like, may be performed on the tapered section of the outer circumferential surface 9c of the fixing ring 9.

The tapered section of the outer circumferential surface 9c of the fixing ring 9 may be a continuous inclined surface or may have a stepped shape. The inclination angle of the tapered section of the outer circumferential surface of the fixing ring 9 with respect to the central axis of the fixing ring 9 may be constant.

The air supply conduit 6 and the air suction conduit 7 can shift air supply and air suction by shifting connection of a pipeline with respect to the pneumoperitoneum apparatus or the suction apparatus. The smoke that disturbs observation or the like of the treatment target portion can be effectively removed in this case as well.

The air supply conduit 6 and the air suction conduit 7 may not be provided.

One through-hole through which the air supply conduit 6 and the air suction conduit 7 are collectively inserted may be formed in the faceplate 2. A through-hole through which the air supply conduit 6 is inserted and a through-hole through which the air suction conduit 7 is inserted may be individually formed in the faceplate 2.

Figure 6:
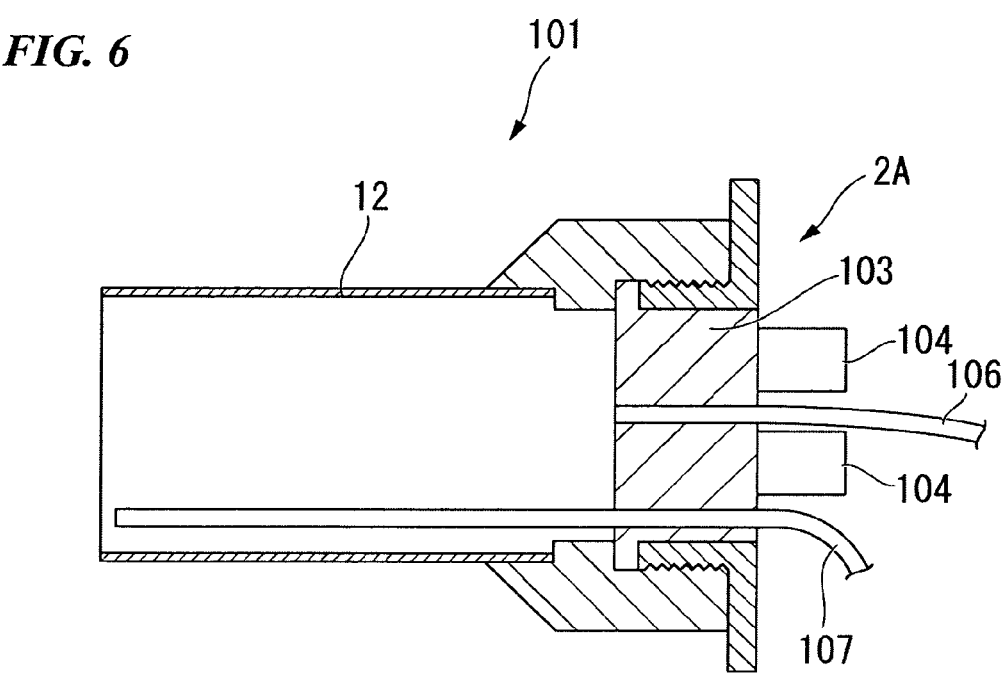
FIG. 6 is a cross-sectional view showing a reference example of the medical port.
Figure 7:
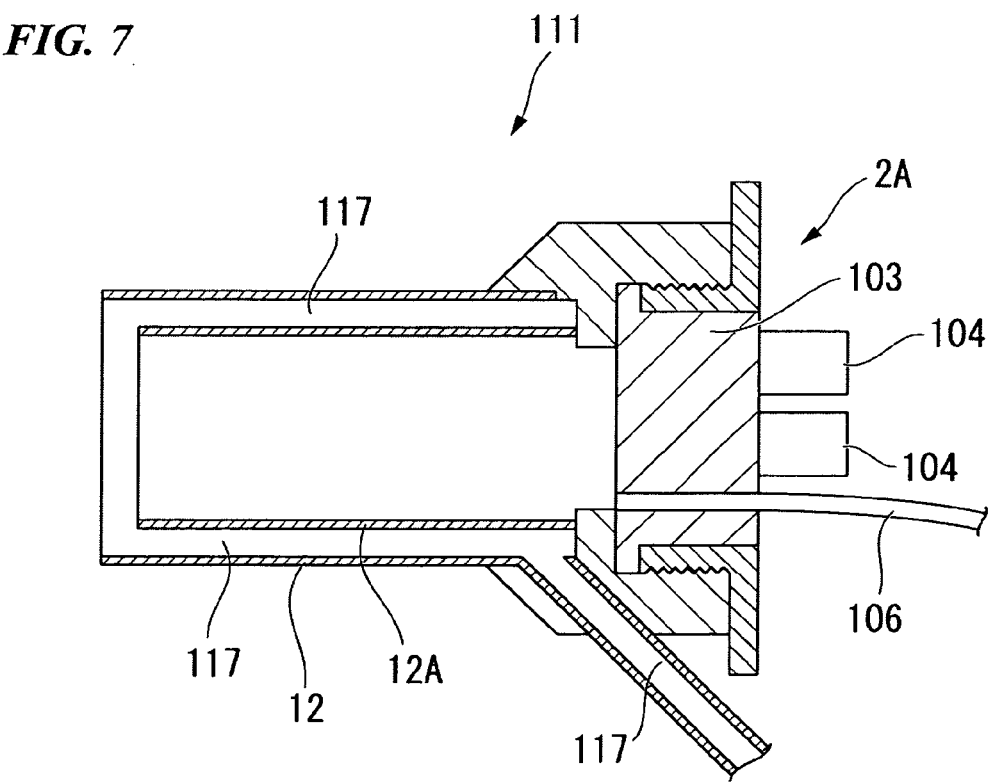
FIG. 7 is a cross-sectional view showing another reference example of the medical port.

Next, another constitution of the medical port is exemplified as a reference. FIG. 6 is a schematic view showing a reference example of the medical port. FIG. 7 is a schematic view showing another reference example of the medical port.

(First Reference Example)

In the present reference example, as shown in FIG. 6, a medical port 101 includes a sheath 12 and a faceplate 2A. The sheath 12 is formed of a material harder than that of the tubular member described in the above-mentioned embodiment. The faceplate 2A is formed at one end of the sheath 12. The faceplate 2A includes a main body 103, a port section 104, an air supply conduit 106 and an air suction conduit 107. A device insertion hole (not shown) in communication with inner and outer portions of the sheath 12 is formed in the port section 104. The sheath 12 of the present reference example has a hardness of an extent to which the sheath is maintained in a tubular shape by itself in a normal use state. Further, the air supply conduit 106 is opened at a surface of the faceplate 2A facing the sheath 12. The air suction conduit 107 is fixed to the inner surface of the sheath 12 and opened at an opening end of the sheath 12 (an end opposite the side at which the faceplate 2A is disposed).

The faceplate 2A is distinguished from the faceplate according to the embodiment in that there is no need for a gap configured to extract the tubular member, which is the moving member 10 described in the embodiment.

The gas can be circulated in the rectum, and the smoke or stem caused by incision or the like in the rectum can be appropriately exhausted in the above-mentioned constitution as well.

(Second Reference Example)

As shown in FIG. 7, in the present reference example, a medical port 111 is distinguished from the medical port according to the embodiment in that an inner sheath 12A inserted into the sheath 12 is provided in addition to the sheath 12 described in the first reference example.

A gap is opened between the sheath 12 and the inner sheath 12A. Further, the gap between the sheath 12 and the inner sheath 12A functions as an air suction conduit 117. In addition, the gap between the sheath 12 and the inner sheath 12A may function as an air supply conduit.

In the present reference example, when the gap between the sheath 12 and the inner sheath 12A is used as the air suction conduit 117, the gas can also be suctioned from all positions of the entire circumference of the sheath 12. Then, when the medical port 111 is inserted into the rectum, in a center of the rectum, the gas is supplied into the middle of the rectum, and in the vicinity of a wall surface of the rectum, the gas is circulated in the rectum such that the gas flows from the middle of the rectum toward the air suction conduit 117.

In the case of the present reference example, when a treatment such as making an incision throughout the entire circumference of the inner wall of the rectum is performed, the smoke or steam generated by the treatment can be rapidly suctioned into the suction conduit.

(Needle Holder)

Next, a needle holder used with the medical port according to the above-mentioned embodiment and the medical port of each modified example is described.

(First Constitution Example)

Figure 8:
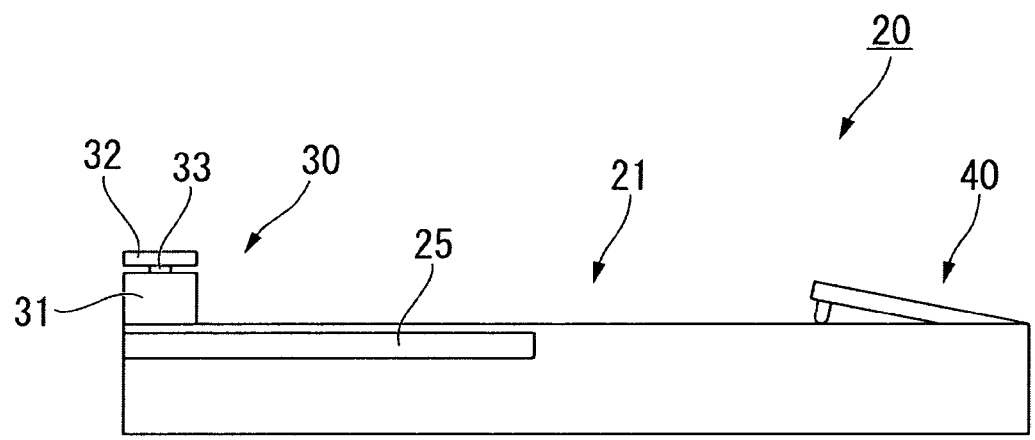
FIG. 8 is a side view of a needle holder used with the medical port.
Figure 9:
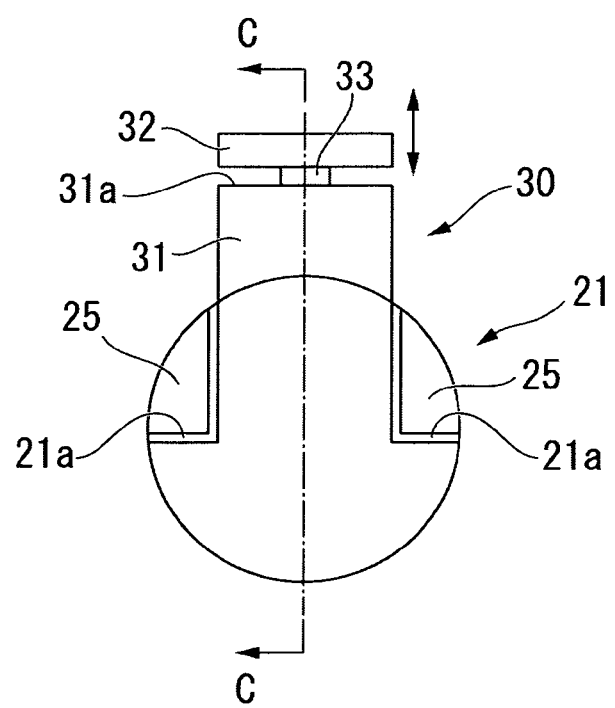
FIG. 9 is a front view of the needle holder.
Figure 10:
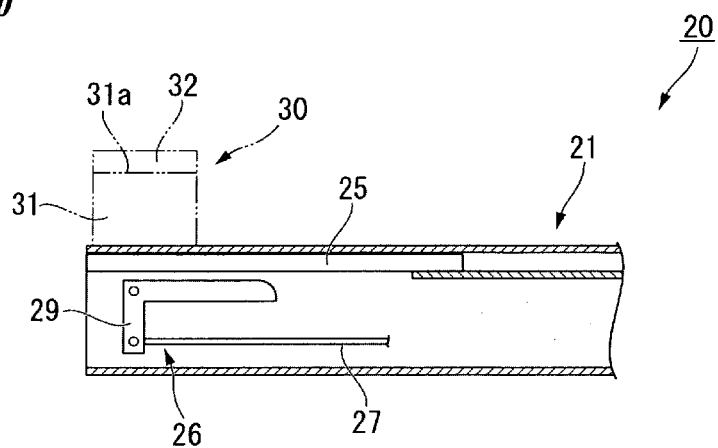
FIG. 10 is a partial cross-sectional view taken along a line C-C of FIG. 9, showing an internal structure of the needle holder.
Figure 11:
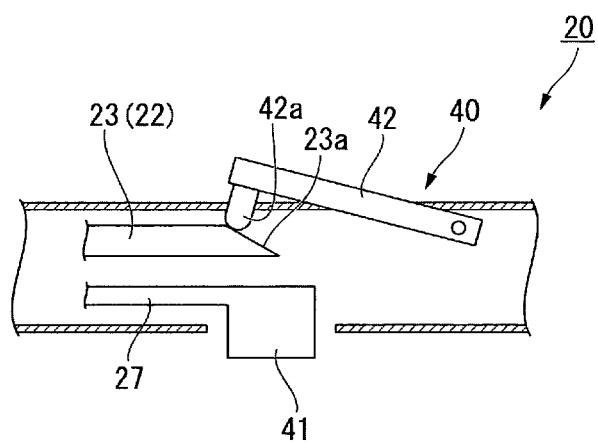
FIG. 11 is a partial cross-sectional view taken along a line C-C of FIG. 9, showing the internal structure of the needle holder.
Figure 12:
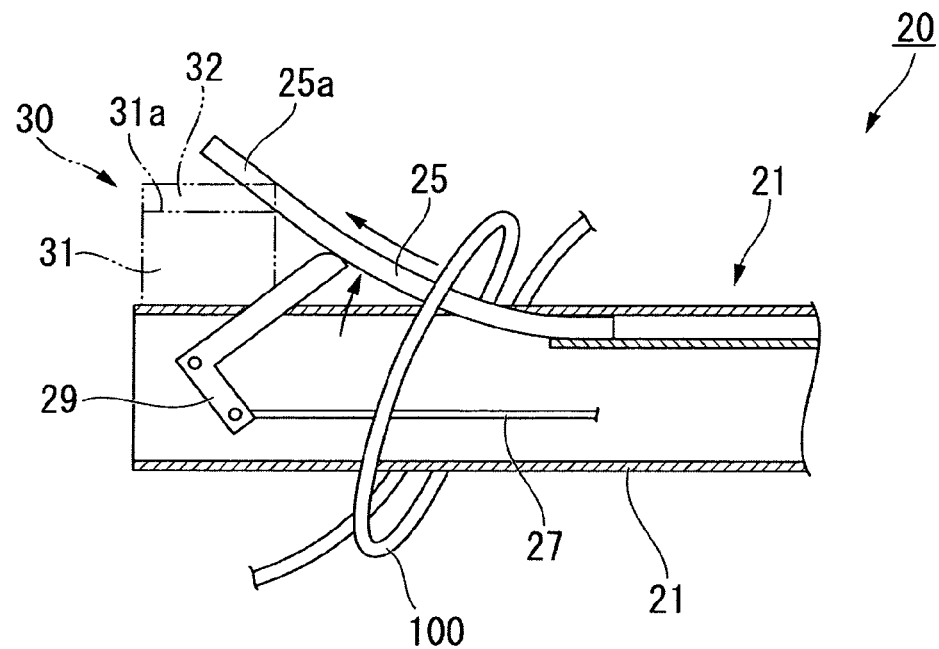
FIG. 12 is an explanatory view showing an operation of the needle holder.

First, a first constitution example of the needle holder is described. FIG. 8 is a side view showing a needle holder that can be used with the medical port. FIG. 9 is a front view of the needle holder. FIG. 10 is a partial cross-sectional view showing an internal structure of the needle holder. FIG. 11 is a partial cross-sectional view showing the internal structure of the needle holder. FIG. 12 is an explanatory view showing an operation of the needle holder.

A needle holder 20 includes an insertion section 21, a treatment section 30 disposed at one end of the insertion section 21, and a manipulation section 40 disposed at the other end of the insertion section 21.

The insertion section 21 is a tubular member having a predetermined length. A power transmission unit 22 (a manipulation rod 23 and a manipulation link (not shown)) configured to move the treatment section 30 by manipulation of the manipulation section 40 is disposed in the insertion section 21. In addition, an elastic body 25, an uplift mechanism 26, and an accommodating section 21a are provided at the insertion section 21. The elastic body 25 is disposed to be parallel to a central axis of the insertion section 21. The uplift mechanism 26 is configured to deform the elastic body 25 into a curved shape. The accommodating section 21a is formed at the outer surface of the insertion section 21, and the elastic body 25 is accommodated in the accommodating section 21a.

The elastic body 25 is a rod-shaped member accommodated in the accommodating section 21a in parallel with the central axis of the insertion section 21 when no external force is applied thereto. In addition, the elastic body 25 is fixed to the insertion section 21 at an end thereof near the manipulation section 40. An end of the elastic body 25 near the treatment section 30 is not fixed to the insertion section 21. Further, the elastic body 25 is configured to be elastically deformed into a curved shape with respect to the central axis of the insertion section 21 by the uplift mechanism 26.

The uplift mechanism 26 has an uplift rod 27, a slide knob 41, and an uplift link 29. The uplift rod 27 is disposed in the insertion section 21 so as to advance and retract in a direction of the central axis of the insertion section 21. The slide knob 41 is fixed to the uplift rod 27 in the manipulation section 40. The uplift link 29 is coupled to the uplift rod 27 in the treatment section 30.

The uplift mechanism 26 rotates the uplift link 29 about a predetermined rotation shaft when the uplift rod 27 is pulled toward the manipulation section 40. Accordingly, the uplift link 29 is in contact with the elastic body 25, and further, an end section of the elastic body 25 near the treatment section 30 is pressed. As a result, as the uplift link 29 is rotated about the rotation shaft, the elastic body 25 is elastically deformed into a curved state. Here, an end of the elastic body 25 near the treatment section 30 is moved to a position adjacent to the ring member 32 (to be described below) of the treatment section 30 by the uplift link 29.

In the present constitution example, the elastic body 25, the uplift link 29, and the uplift rod 27 are disposed at two places spaced apart from each other so as to sandwich the treatment section 30 therebetween. Further, one slide knob 41 is provided with respect to two uplift rods 27. As the one slide knob 41 advances and retracts, the two uplift rods 27 can also similarly move to advance and retract.

The treatment section 30 includes a pipe section 31, the ring member 32, and a pin 33. The pipe section 31 protrudes in a direction perpendicular to the central axis of the insertion section 21 at one end of the insertion section 21 (which is opposite to an end of a side at which the manipulation section 40 is provided, and is a distal end during use of the needle holder 20). The ring member 32 is disposed so as to come in contact with a protrusion end surface 31a of the pipe section 31. The pin 33 is fixed to the ring member 32, and is inserted into the pipe section 31.

The ring member 32 advances and retracts in a direction of the central axis of the pipe section 31 by the pin 33. The ring member 32 can sandwich the surgical needle between the protrusion end surface 31a of the pipe section 31 and the ring member 32 to hold the surgical needle.

The manipulation rod 23 and the manipulation link (not shown) are provided in the insertion section 21. The manipulation rod 23 is advanced and retracted in the direction of the central axis of the insertion section 21. The manipulation link is configured to convert the advance and retraction movement of the manipulation rod 23 into linear movement of the pin 33. In addition, a manipulation knob 42 configured to advance and retract the manipulation rod 23 in the direction of the central axis of the insertion section 21 is formed in the manipulation section 40.

The manipulation rod 23 has an inclination end surface 23a inclined with respect to the central axis of the insertion section 21 in the manipulation section 40. The manipulation knob 42 has an abutting protrusion 42a in contact with the inclination end surface 23a of the manipulation rod 23 in a direction perpendicular to the central axis of the insertion section 21. Accordingly, when the manipulation knob 42 is manipulated, the abutting protrusion 42a comes in contact with the inclination end surface 23a, and the manipulation rod 23 is moved toward the treatment section 30. On the other hand, when the abutting protrusion 42a is separated from the inclination end surface 23a, the manipulation rod 23 is moved toward the manipulation section 40.

When the manipulation rod 23 is moved, the movement of the manipulation rod 23 is converted into linear movement of the pin 33. Accordingly, as the manipulation knob 42 is manipulated, the protrusion end surface 31a of the pipe section 31 and the ring member 32 can approach each other or be separated from each other.

Constitutions of the treatment section 30 and the manipulation section 40 can appropriately employ components of a needle driver disclosed in the description of PCT International Publication No. WO 2004/066848.

For example, the needle holder 20 of the present constitution example is used when the biological tissue is sutured after incision of the biological tissue in the rectum using the medical port 1 according to the embodiment.

When the needle holder 20 of the present constitution example is used, the user inserts the needle holder 20 into the device insertion hole 5 of the medical port 1 using the treatment section 30 side as a distal end. Here, the needle holder 20 is guided to the treatment target portion in a state in which the surgical needle and a suture thread 100 are attached to the treatment section 30 of the needle holder 20. In addition, as necessary, the medical devices are appropriately inserted into other device insertion holes 5 to perform the treatment.

In the present constitution example, in a place at which the user's hand does not directly reach, the user sutures the treatment target portion using the needle holder 20. In the treatment section 30 of the needle holder 20, the pipe section 31 protrudes in a direction perpendicular to the central axis of the insertion section 21. For this reason, the needle holder 20 holds the medical needle in a positional relation at which the biological tissue can be easily sutured in the direction of the central axis of the insertion section 21.

After the thread passes through the biological tissue, the user sutures the biological tissue in the rectum using the needle holder 20 and, for example, a gripping forceps configured to grip the suture thread 100. The user ties the suture thread 100 in a surgical knot. In this case, the suture thread 100 is wound on the insertion section 21 of the needle holder 20 by several turns, and the other end side of the suture thread 100 is inserted into a loop of the suture thread 100 wound on the needle holder 20 to perform suturing.

In the needle holder 20 of the present constitution example, before the suture thread 100 is wound on the needle holder 20, the slide knob 41 of the manipulation section 40 is manipulated, and the uplift rod 27 is moved toward the manipulation section 40. Accordingly, the elastic body 25 is deformed into a curved shape by the uplift link 29. Therefore, an inclined surface 25a by the elastic body 25 extending from the outer surface of the insertion section 21 toward the ring member 32 is formed at the insertion section 21.

Accordingly, when the insertion section 21 is pulled out from a circle of the suture thread 100 wound on the outer surface of the insertion section 21, the suture thread 100 is guided from the outer surface of the insertion section 21 to the ring member 32 by the inclined surface 25a formed by the elastic body 25. For this reason, the suture thread 100 is smoothly removed from the needle holder 20 without the suture thread 100 being caught by the pipe section 31.

As described above, according to the needle holder 20 of the present constitution example, the suture thread 100 can be prevented from being caught by the treatment section 30 when the biological tissue is sutured by the surgical knot.

In the related art, when the suture thread is caught by the treatment section, there is a need to remove the suture thread from the treatment section using separate medical devices such as a gripping forceps and so on. In this case, when the number of medical devices that can be simultaneously used as in treatment through the medical port 1 is limited, a procedure may be complicated. However, in the case of the present constitution example, since there is no need to use the other medical devices, the biological tissue can be easily sutured.

(Second Constitution Example)

Figure 13:
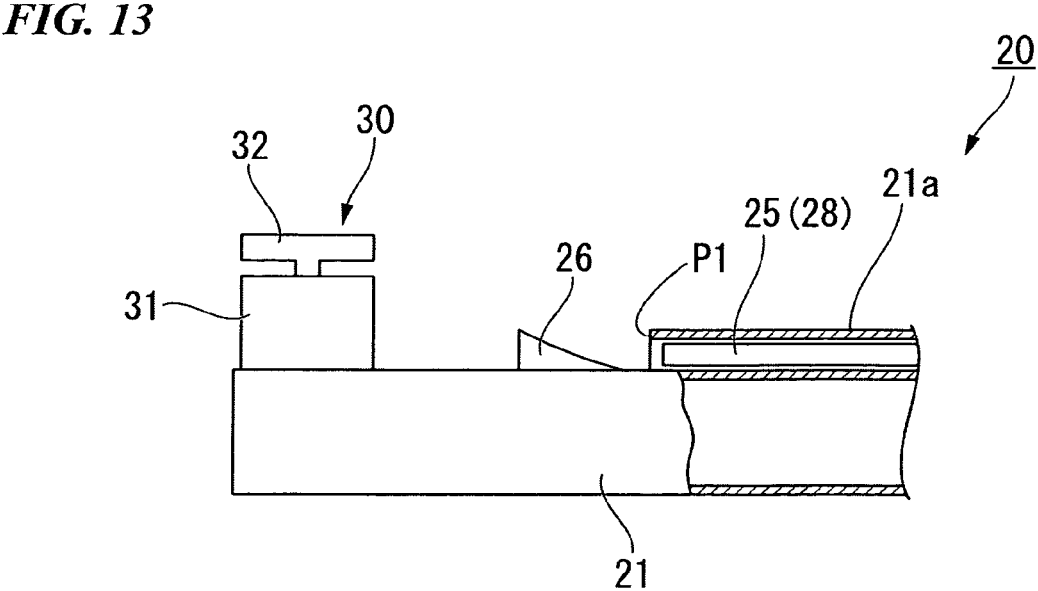
FIG. 13 is a partial cross-sectional view showing another constitution example of the needle holder used with the medical port.
Figure 14:
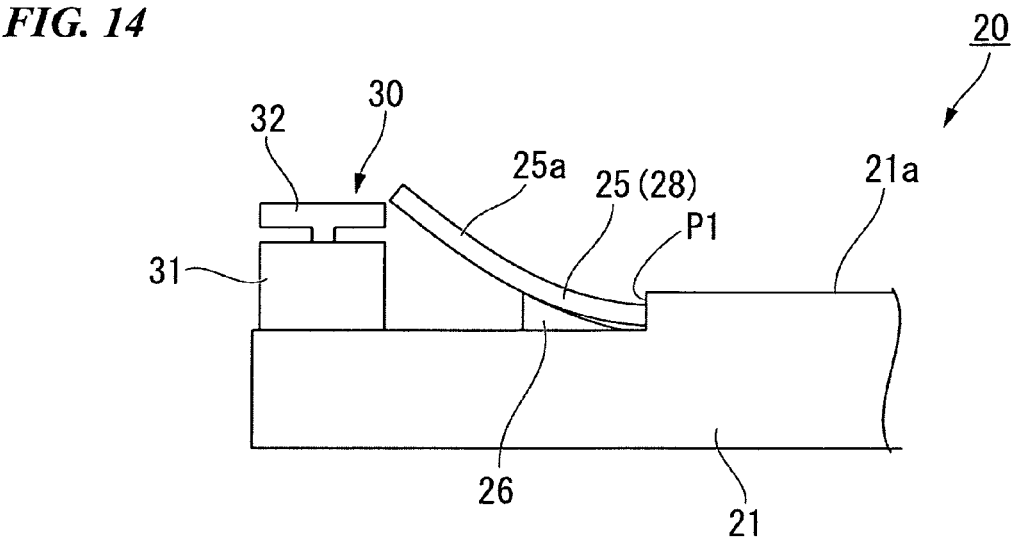
FIG. 14 is an explanatory view showing an operation of the needle holder.

Next, a second constitution example of the needle holder 20 is described. FIG. 13 is a partial cross-sectional view showing a needle holder of the present constitution example. FIG. 14 is an explanatory view showing an operation of the needle holder of the present constitution example.

In the present constitution example, the constitutions of the elastic body 25 and the uplift mechanism 26 are different from those of the first constitution example.

As shown in FIGS. 13 and 14, in the present constitution example, the elastic body 25 is constituted by an elastic rod 28 that can advance and retract in the direction of the central axis of the insertion section 21. In addition, the accommodating section 21a configured to accommodate the elastic body 25 is formed in a tubular shape having an opening at a position P1 which is at a distal end side of the insertion section 21 and is spaced a predetermined distance from the treatment section 30 toward a proximal end of the insertion section 21.

The uplift mechanism 26 is constituted by a protrusion which is formed between the position P1 and the treatment section 30 and is inclined from the outer surface of the insertion section 21 toward the ring member 32.

The slide knob 41 described in the first constitution example is attached to an end of the elastic body 25 near the manipulation section 40.

In the present constitution example, as the elastic body 25 is moved toward the distal end of the insertion section 21, the elastic body 25 comes in contact with the protrusion, which is the uplift mechanism 26. The distal end of the elastic body 25 is deformed to be directed toward the ring member 32 by the protrusion, which is the uplift mechanism 26. Accordingly, the inclined surface 25a by the elastic body 25 extending from the outer surface of the insertion section 21 toward the ring member 32 is formed at the insertion section 21.

In the above-mentioned constitution, the same effect as the first constitution example is exhibited.

The structure is simple in comparison with the first constitution example using the uplift link 29, and easy manufacture becomes possible and malfunctions are rare.

Figure 15:
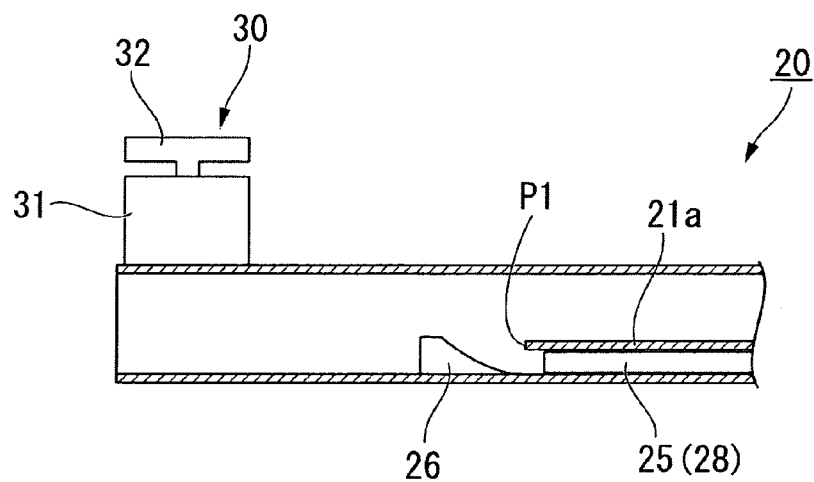
FIG. 15 is a partial cross-sectional view showing still another constitution example of the needle holder used with the medical port.
Figure 16:
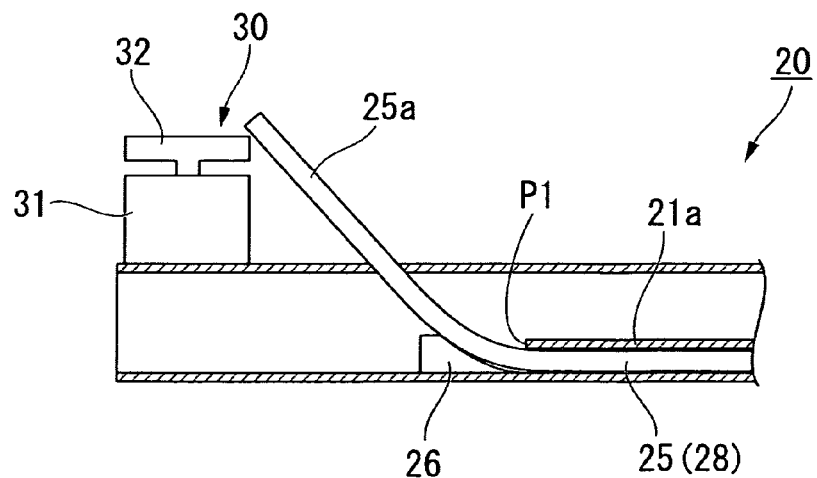
FIG. 16 is an explanatory view showing an operation of the needle holder.

A modified example of the present constitution example is described with reference to FIGS. 15 and 16. FIG. 15 is a partial cross-sectional view showing a needle holder of the modified example of the present constitution example. FIG. 16 is an explanatory view showing an operation of the needle holder of the modified example of the present constitution example.

As shown in FIGS. 15 and 16, for example, both of the protrusion, which is the uplift mechanism 26, and the elastic rod 28 are disposed in the insertion section 21. The above-mentioned effect is exhibited in this case as well.

(Third Constitution Example)

Figure 17:
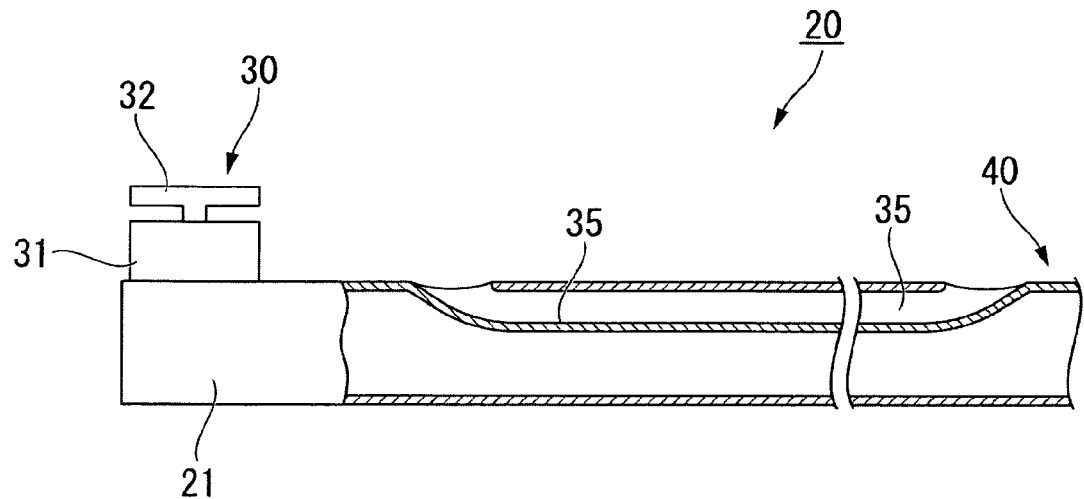
FIG. 17 is a partial cross-sectional view showing still another constitution example of the needle holder used with the medical port.
Figure 18:
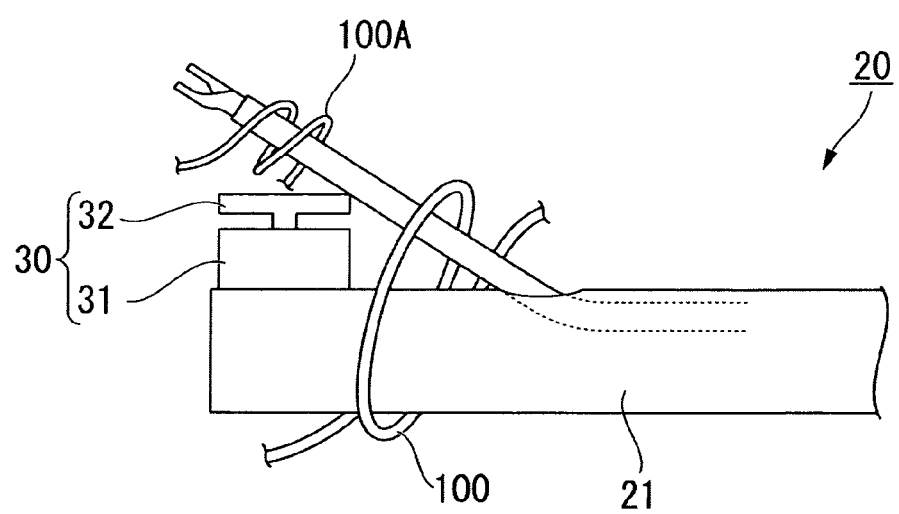
FIG. 18 is an explanatory view showing an operation of the needle holder.

Next, a third constitution example of the needle holder 20 is described. FIG. 17 is a partial cross-sectional view showing a needle holder of the present constitution example. FIG. 18 is an explanatory view showing an operation of the needle holder of the present constitution example.

As shown in FIGS. 17 and 18, the needle holder 20 of the present constitution example is distinguished from the above constitution examples in that a channel 35 opened toward the treatment section 30 and the manipulation section 40 is formed at the insertion section 21. The opening disposed near the treatment section 30 in the openings of the channel 35 is directed from the outer surface of the insertion section 21 toward the ring member 32.

In the present constitution example, a gripping forceps for a conventional endoscope or the like can be inserted into the channel 35. For example, when the gripping forceps is inserted through the channel 35 to be used, the gripping forceps protruding from the opening of the channel 35 near the treatment section 30 protrudes from the outer surface of the insertion section 21 toward the ring member 32 in a direction crossing the central axis of the insertion section 21, i.e., in a direction inclined forward with respect to the insertion section 21.

The user can wind the suture thread 100 on the insertion section 21. In addition, as another suturing method, a suture thread 100A can be wound on the gripping forceps protruding from the channel 35. Accordingly; the same effect as the first and second constitution examples is exhibited. In addition, since a portion of the gripping forceps on which the suture thread 100 can be wound extends forward to be inclined with respect to the insertion section 21, tying using the suture thread 100 can be easily performed.

(Fourth Constitution Example)

Figure 19:
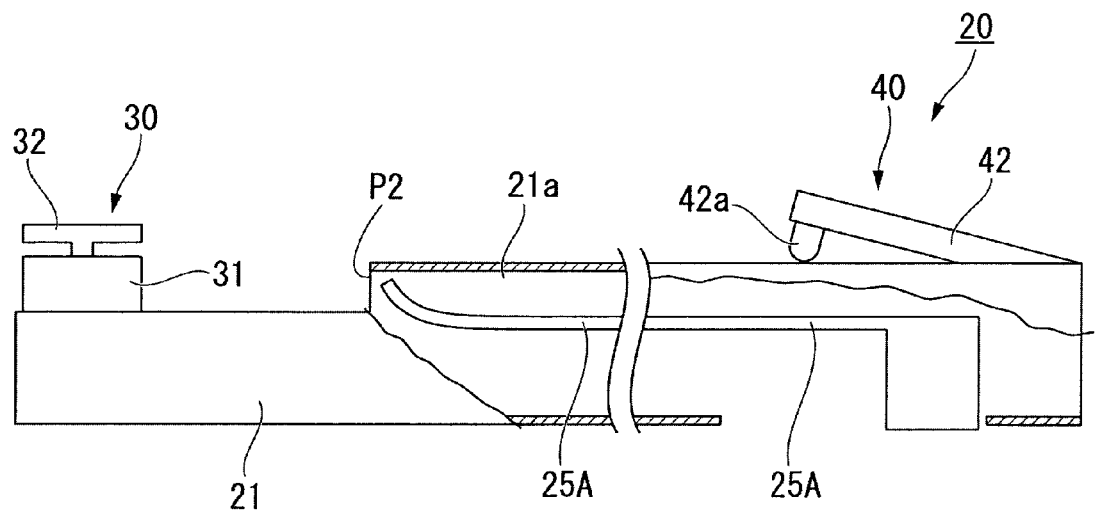
FIG. 19 is a partial cross-sectional view showing still another constitution example of the needle holder used with the medical port.
Figure 20:
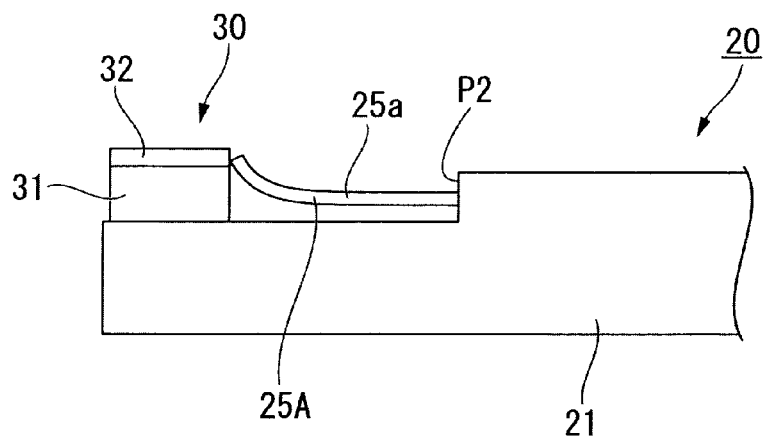
FIG. 20 is an explanatory view showing an operation of the needle holder.

Next, a fourth constitution example of the needle holder 20 is described. FIG. 19 is a partial cross-sectional view showing a needle holder of the present constitution example. FIG. 20 is an explanatory view showing an operation of the needle holder of the present constitution example.

As shown in FIGS. 19 and 20, the needle holder 20 of the present constitution example is distinguished from the above constitution examples in that an elastic body 25A having a different shape is provided instead of the elastic body 25.

The elastic body 25A is formed in a previously curved shape to extend in parallel to the insertion section 21 at the manipulation section 40 side and extend in a direction crossing the central axis of the insertion section 21 at the treatment section 30 side. In addition, the elastic body 25A is configured to advance and retract in the direction of the central axis of the insertion section 21. Further, in the insertion section 21, an opening configured to protrude the elastic body 25A is formed at a position P2 spaced a predetermined distance from the treatment section 30 towards the manipulation section 40.

In the present constitution example, in a state in which the elastic body 25A is accommodated in the opening, the elastic body 25A is pressed by the inner surface of the insertion section 21 to be elastically deformed. When the elastic body 25A protrudes from the opening of the insertion section 21, the elastic body 25A returns to its original curved shape due to elasticity of the elastic body 25A itself. The elastic body 25A is moved to a position at which the distal end of the elastic body 25A abuts the ring member 32. Accordingly, the inclined surface 25a inclined from the outer surface of the insertion section 21 toward the ring member 32 is formed by the elastic body 25A.

In the present constitution example, when the elastic body 25A is accommodated in the opening of the insertion section 21, the elastic body 25A is accommodated in an elongated state or in a downwardly pushed state. For this reason, the insertion section 21 can be reduced in diameter in comparison with the case in which the curved elastic body 25A is drawn into the insertion section 21 as it is. Even in the elastic body 25A extended and accommodated as described above, when the elastic body 25A protrudes from the opening of the insertion section 21, like each of the above constitution examples, the inclined surface 25a is formed from the outer surface of the insertion section 21 toward the ring member 32.

(Fifth Constitution Example)

Figure 21:
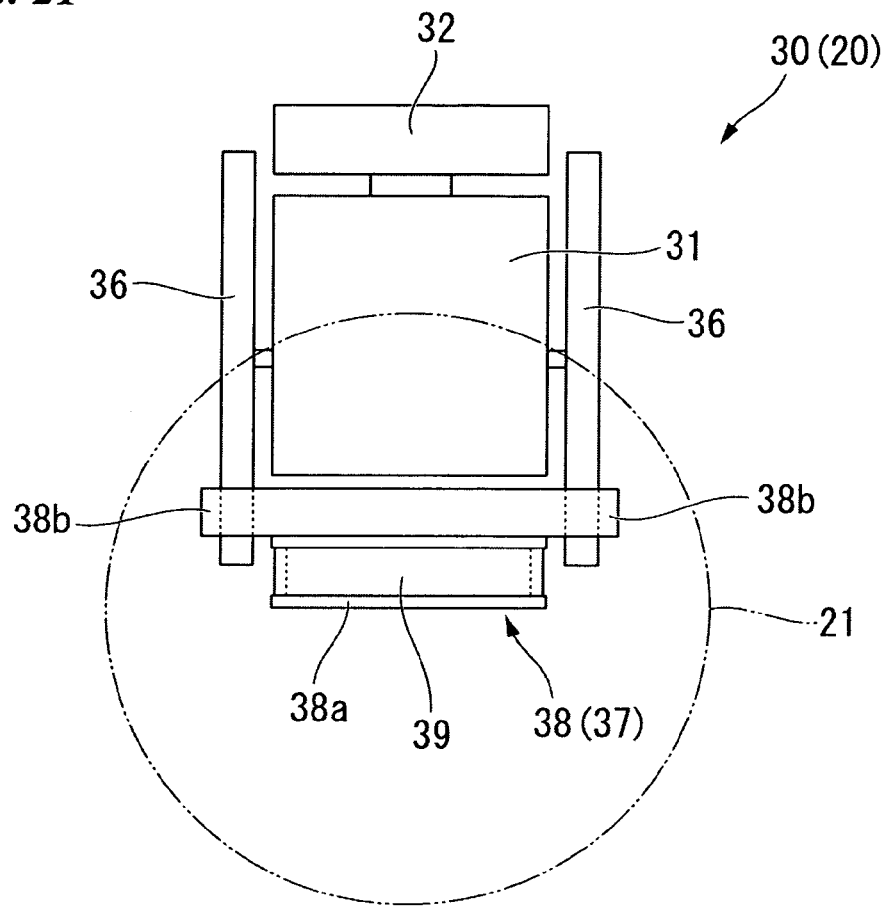
FIG. 21 is a front view showing a partial constitution of still another example of the needle holder used with the medical port.

Next, a fifth constitution example of the needle holder 20 is described. FIG. 21 is a front view showing a constitution of a portion of a needle holder of the present constitution example.

Figure 22:
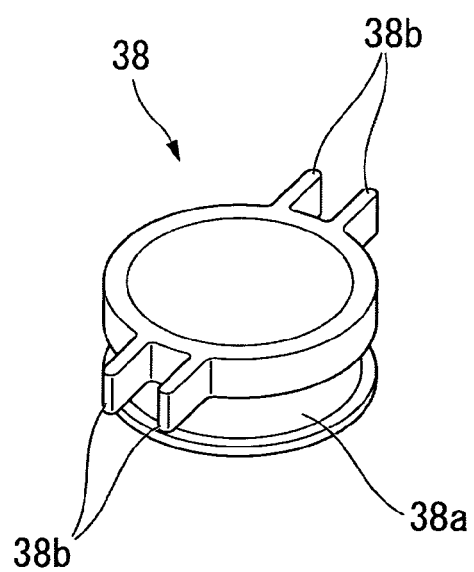
FIG. 22 is a perspective view showing a rotation link mounted on the needle holder.
Figure 23:
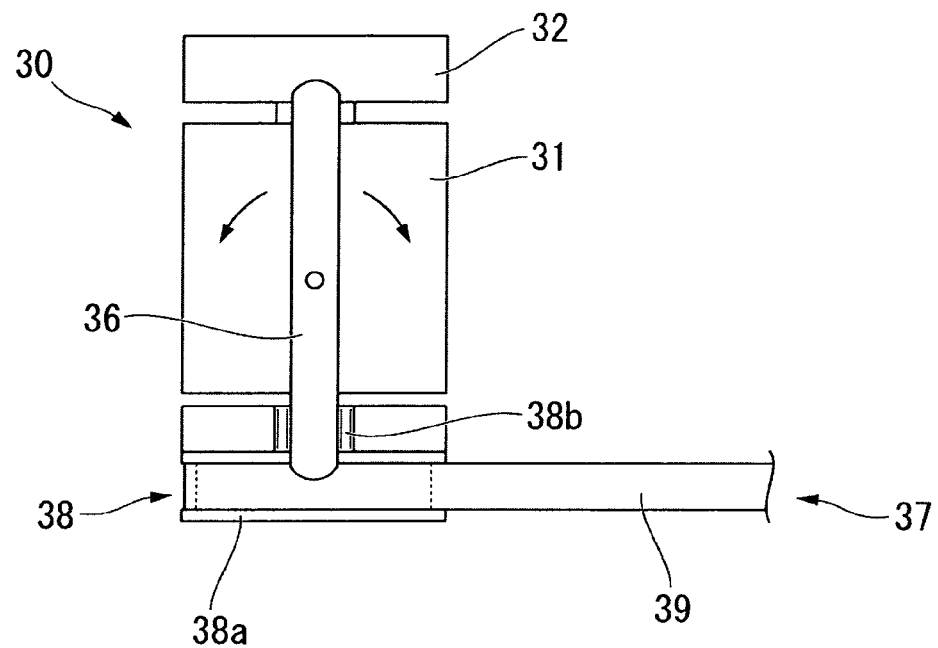
FIG. 23 is a side view showing a partial constitution of the needle holder.
Figure 24:
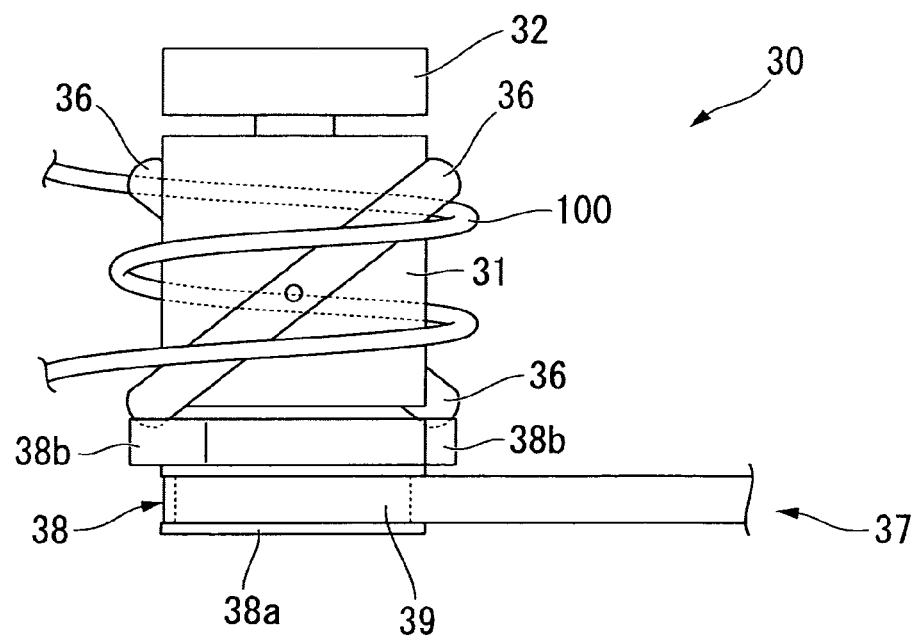
FIG. 24 is an explanatory view showing an operation of the needle holder.

FIG. 22 is a perspective view showing a rotation link mounted on the needle holder of the present constitution example. FIG. 23 is a side view showing a constitution of a portion of the needle holder of the present constitution example. FIG. 24 is an explanatory view showing an operation of the needle holder of the present constitution example.

As shown in FIGS. 21 to 23, the needle holder 20 of the present constitution example is distinguished from the above constitution examples in that thread locking members 36 and a driving mechanism 37 are provided instead of the elastic body 25. The thread locking members 36 are disposed at two places to sandwich the pipe section 31 therebetween. The driving mechanism 37 is configured to drive each of the thread locking members 36.

Each of the thread locking members 36 is configured to be rotatable about an axis perpendicular to the central axis of the pipe section 31 as a rotation shaft. One end of each of the thread locking members 36 is disposed at the ring member 32 side. The other end of each of the thread locking members 36 is disposed in the insertion section 21.

A rotation link 38 and a rotation belt 39 are provided in the insertion section 21. The rotation link 38 is locked by both of the two thread locking members 36. The rotation belt 39 is configured to rotate the rotation link 38 by manipulation in the manipulation section 40.

The rotation link 38 has a pulley section 38a and a locking protrusion section 38b. The rotation belt 39 (to be described below) is hung around the pulley section 38a. The locking protrusion section 38b protrudes from the outer circumference of the pulley section 38a toward the outside in the radial direction of the pulley section 38a. The rotation shaft of the rotation link 38 is configured with the same axis as the central axis of the pipe section 31.

The rotation belt 39 formed in an endless belt shape is hung around the pulley section 38a. In addition, the rotation belt 39 is also hung around the other pulley (not shown) provided in the manipulation section 40. A unit configured to advance and retract the endless belt in the direction of the central axis of the insertion section 21 or a unit configured to rotate the pulley (not shown) provided in the manipulation section 40 is provided in the manipulation section 40.

The locking protrusion sections 38b are formed at two places opposite to each other in the outer circumferential surface of the rotation link 38. Each of the locking protrusion sections 38b has a concave section into which the thread locking member 36 is inserted. Accordingly, when the rotation link 38 is rotated, each of the thread locking members 36 inserted into the concave section is rotated about the rotation shaft of each of the thread locking members 36. Here, one ends of the thread locking members 36 are moved in opposite directions such that one is moved toward the distal end of the insertion section 21 and the other is moved toward the proximal end of the insertion section 21 (see FIG. 24). Accordingly, when seen from the direction of the rotation shaft of each of the thread locking members 36, a positional relation of the thread locking members 36 is varied by rotation of the rotation link 38 in any one of a state in which the thread locking members 36 cross each other in an X shape and a state in which the thread locking members 36 are parallel to the central axis of the pipe section 31.

In the present constitution example, as shown in FIG. 24, when the thread locking members 36 are disposed in the X shape, the user can tie the suture thread 100 to the pipe section 31. Here, the suture thread 100 is prevented from being drawn from the pipe section 31 by one end of each of the thread locking members 36 (an end disposed at the ring member 32 side). Then, as the thread locking members 36 are parallel to the central axis of the pipe section 31, the suture thread 100 can be drawn from the pipe section 31.

In the present constitution example, since the suture thread 100 can be wound on the pipe section 31 having a central axis extending in a direction perpendicular to the central axis of the insertion section 21, the suture thread 100 can be easily wound.

Hereinabove, while preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the appended claims.

What is claimed is:

1. A medical port comprising:
    a faceplate including:
        a main body having a disc shape, wherein a through-hole through which a medical device is configured to be inserted is formed in the main body, and
        a fixing plate connected to the main body such that a gap in the faceplate is formed between the fixing plate and an outer circumferential surface of the main body in a state in which movement of the fixing plate with respect to the main body in a direction along a central axis of the faceplate is restricted;
    a fixing ring being formed in an annular shape and having:
        an internal space into which the medical device passing through the through-hole is configured to be inserted,
        a first opening end which is in communication with the internal space and is opened at a faceplate side,
        a second opening end which is in communication with the internal space and is opened at a side opposite to the faceplate side,
        a tapered section having a first portion that has a predetermined outer diameter and is formed in a side of the first opening end in a radial direction with respect to the central axis of the faceplate, and a second portion that has an outer diameter larger than the predetermined outer diameter of the first portion and is formed in a side of the second opening end in the radial direction, and
        an outer circumferential surface having an outer diameter that gradually increases from the first opening end toward the second opening end; and
    a moving member being a flexible tubular member and being formed in a double tube shape in which an inner surface and an outer surface are turned to be interchanged at a halfway portion in an extending direction of the moving member, the moving member having:
        a first end that is fixed to any one of the fixing plate and the main body,
        a first tube that is one of an inner tube and an outer tube of the moving member and that includes the first end of the moving member, and
        a second tube that is the other of the inner tube and the outer tube, that does not include the first end of the moving member, and that is inserted into the gap in the faceplate,
    wherein:
    the fixing ring has a first thickness in the radial direction at the side of the first opening end and a second thickness in the radial direction at the side of the second opening end, the second thickness being larger than the first thickness,
    the fixing ring is disposed in a space between the first tube and the second tube, and
    the fixing ring is configured to move toward the faceplate along the central axis of the faceplate to sandwich a lumen of a living body tissue with the faceplate by the second tube inserted into the gap in the faceplate being pulled to fix the medical port to the lumen of the living tissue.

2. The medical port according to claim 1, wherein an inner diameter of at least one of the first opening end and the second opening end is smaller than an outer diameter of the faceplate.

3. The medical port according to claim 1, wherein the fixing ring is elastically deformable.

4. The medical port according to claim 1, wherein:
    an air supply conduit and an air suction conduit are formed in the through-hole of the main body and extend substantially parallel to the central axis of the faceplate, and
    a position of an opening of the air supply conduit directed in a direction from the faceplate toward the fixing ring and a position of an opening of the air suction conduit directed in the direction from the faceplate toward the fixing ring are offset to each other in a direction along the central axis of the faceplate.

5. The medical port according to claim 1, wherein the internal space of the fixing ring has a constant diameter in a longitudinal direction of the fixing ring.

6. The medical port according to claim 5, wherein the outer circumferential surface of the fixing ring and the second tube of the moving member are configured to contact and conform to an inner diameter of an anus of a living body when the medical port is in use.

* * * * *